United States Patent [19]

Doyle

[11] Patent Number: 5,015,100

[45] Date of Patent: May 14, 1991

[54] APPARATUS AND METHOD FOR NORMAL INCIDENCE REFLECTANCE SPECTROSCOPY

[75] Inventor: Walter M. Doyle, Laguna Beach, Calif.

[73] Assignee: Axiom Analytical, Inc., Laguna Beach, Calif.

[21] Appl. No.: 487,633

[22] Filed: Mar. 2, 1990

[51] Int. Cl.$^5$ .............................................. G01N 21/55
[52] U.S. Cl. ..................................... 356/445; 350/527
[58] Field of Search ............... 356/445, 447, 448, 346; 350/1.2, 172, 523, 527

[56] References Cited

U.S. PATENT DOCUMENTS

| | | | |
|---|---|---|---|
| 4,479,700 | 10/1984 | Abe | 350/523 |
| 4,712,912 | 12/1987 | Messerschmidt | 356/445 |
| 4,758,088 | 7/1988 | Doyle | 350/527 |
| 4,852,955 | 8/1989 | Doyle et al. | 350/622 |

Primary Examiner—Richard A. Rosenberger
Attorney, Agent, or Firm—Thomas J. Plante

[57] ABSTRACT

An external reflectance spectroscopy apparatus and method are disclosed in which maximum radiation throughput is obtained by using a beamsplitter which reflects half of a collimated beam and transmits the other half. In order to obtain reliable results, the condition of perpendicular incidence on the sample is approximated (without limiting throughput) by providing a beamsplitter having an uneven number of reflecting blades and the same number of transmitting openings. Each reflecting blade is opposite to an open area having the same size and shape. The result is a substantial equalizing of contributions from rays polarized parallel to the plane of incidence and from rays polarized perpendicular to the plane of incidence.

15 Claims, 9 Drawing Sheets

APPARATUS AND METHOD FOR NORMAL INCIDENCE REFLECTANCE SPECTROSCOPY

BACKGROUND OF THE INVENTION

This invention relates to spectroscopy, and specifically to external reflectance spectroscopy. It is concerned primarily with a form of reflectance spectroscopy in which chemical structure information about a material is determined directly by monitoring the Fresnel reflectance of the first surface of a dielectric material. It can also be used for what is often called reflection/absorption spectroscopy, in which the analysis is actually accomplished by absorption spectroscopy of a thin layer on a reflecting substrate.

Diffuse reflectance spectroscopy is widely used in the visible and near-infrared regions of the spectrum to study solid materials in their unmodified state. For example, visible diffuse reflectance is used for color analysis; and near-infrared diffuse reflectance is used for studying the physical and chemical properties of grains and other food products.

Diffuse reflectance spectroscopy takes advantage of the fact that most materials contain scattering centers (structural discontinuities) which tend to scatter light in a more or less random fashion. After multiple interactions with such centers, a significant fraction of the light will eventually be scattered back out of the sample. The amplitude of this signal will be dependent on the density of scattering centers, and on any absorption of the radiation by the sample material. By collecting this radiation a quantitative spectrum of the sample is obtained which is somewhat analogous to a conventional absorbance spectrum.

One desirable goal in external reflectance spectroscopy is extending its usefulness to the mid-infrared region. In principle, mid infrared spectroscopy has some marked advantages over visible and near-infrared spectroscopy for the analysis of organic materials. This is due to the fact that the fundamental absorbances of virtually all organic materials lie in the mid-infrared. These materials have very few absorption bands of interest in the visible region. The overtone bands which occur in the near-infrared tend to be broad and overlapping, making positive identification of species extremely difficult. In the mid-infrared region, the absorption bands are generally narrow and distinct, allowing absorbance subtraction and other techniques to be used to distinguish the spectral contributions of various species.

Despite its advantages, mid-infrared has not been widely used for the analysis of intact bulk samples. A primary reason for this is the fact that the mid-infrared properties of most materials are not advantageous for the use of diffuse reflectance. The effectiveness of the scattering centers in diffuse reflectance is inversely proportional to wavelength, so that scattering in the mid-infrared region tends to be relatively weak. At the same time, the fundamental absorbances which occur in this region are very strong. As a result, the signal levels obtained in mid-infrared diffuse reflectance of intact objects are often very weak. In addition, the spectra obtained are often distorted by the presence of first surface (dielectric) reflectance contributions. In the laboratory, this problem is often overcome by grinding the sample and mixing it with a nonabsorbing, scattering substance, such as potassium bromide powder. This approach is not suitable for industrial quality control applications, in which modification of the sample is undesirable.

Attempts have been made to obtain usable mid-infrared spectra of intact solids by such techniques as (a) photo acoustic spectroscopy (PAS), and (b) the use of an integrating sphere to maximize the diffuse signal collected. Neither of these approaches has proved generally acceptable. Integrating spheres tend to produce very low signal levels in the mid-infrared, while PAS is plagued by excess noise and spectral distortions.

An alternative approach to obtaining chemical information about intact samples is to take advantage of the fact that the refractive index, and hence the specular reflectance from the surface, of an organic substance are highly wavelength dependent. The resultant specular reflectance spectra can be used in an manner analogous to absorbance spectra to provide detailed chemical analysis.

The potential utility of specular reflectance spectroscopy (SRS) has been illustrated in recent publications, with particular emphasis on the fact that mathematical expressions called the "Kramers-Kronig relations" can be used to convert measured reflectance spectra into absorbance spectra. These can then be used to identify samples by comparison with existing libraries of absorbance spectra. However, the work reported has not attempted to use SRS for quantitative measurements such as the composition analysis of mixtures of organic substances.

Most of the measurements reported were performed with devices which make use of radiation of unknown polarization state, typically striking the sample with a range of incidence angles other than normal incidence. However, the form of the Kramers-Kronig relations used to perform the data conversion assumes that the radiation is at normal incidence. Thus, the calculated absorbance spectra obtained from such data can be expected to contain spurious angle and polarization dependent artifacts. Indeed such artifacts seem to be evident in some of the reported spectra.

In a paper presented at the FACSS Conference in October, 1989 by Doyle and McIntosh (Paper 424, 16th Annual FACSS Conference), it was concluded that the Kramers-Kronig relations could not be used to obtain accurate absorbance spectra from reflectance data unless the equations used were modified to take into consideration polarization and angle of incidence, or unless the experimental apparatus provided radiation which approximated the conditions at normal incidence.

SUMMARY OF THE INVENTION

The present invention provides an apparatus and method for SRS in which the analytical radiation reflected by the sample approximates the conditions existing at normal incidence of such radiation on the sample.

It is not practical to restrict the range of incidence angles, because that would limit the signal level available for analysis. The solution proposed is to achieve a reasonable approximation of the normal incidence condition by insuring that there are equal contributions from rays polarized parallel to the plane of incidence and from rays polarized perpendicular to the plane of incidence.

While a semi-transparent beamsplitter would achieve the desired polarization balance, such a beamsplitter would sacrifice radiation efficiency. Because of the pre-sample transmission loss, the post-sample reflection loss, and the absorption loss in the beamsplitter, the maximum percentage of entering radiation which could reach the detector, even in the absence of a sample, is, at best, about 16%.

The present invention combines high radiation efficiency with the desired polarization combination by using a split field beamsplitter having at least three radiation reflecting blades separated by three open radiation transmitting areas. Each blade is opposite to an open area, and is equal in size and shape to the opposite area, in order that the radiation reflected by a blade, and then by the sample, will not be blocked on its way to the detector. Other numbers of paired blades and open areas may be used, e.g., five, seven, nine, etc.

BRIEF DESCRIPTION OF DRAWINGS

FIGS. 6-8 show the "split beam" beamsplitter which provides the advantages of the present invention.

DETAILED DESCRIPTION OF SPECIFIC EMBODIMENTS

A theoretical discussion of the problem is needed as a preface to disclosure of the means devised for solving the problem. The object is to use specular reflectance from the surface of a sample as a way of analyzing the sample. As stated above, accomplishing this objective without distortion of the information requires, essentially, that the reflected rays be perpendicular to the plane of the sample surface, or be so distributed that the radiation effectively creates the same reflection effects as if its rays were perpendicular to that plane.

The fraction of the signal reflected when a beam of optical radiation strikes the surface of a flat solid object depends on the angle of incidence, the polarization state of the radiation, and the index of refraction of the target. In general, the refractive index can be thought of as having a real and an imaginary part, where the real part gives rise to the first surface dielectric reflection, and the imaginary part gives rise to the bulk absorption of the material.

Figure 1:
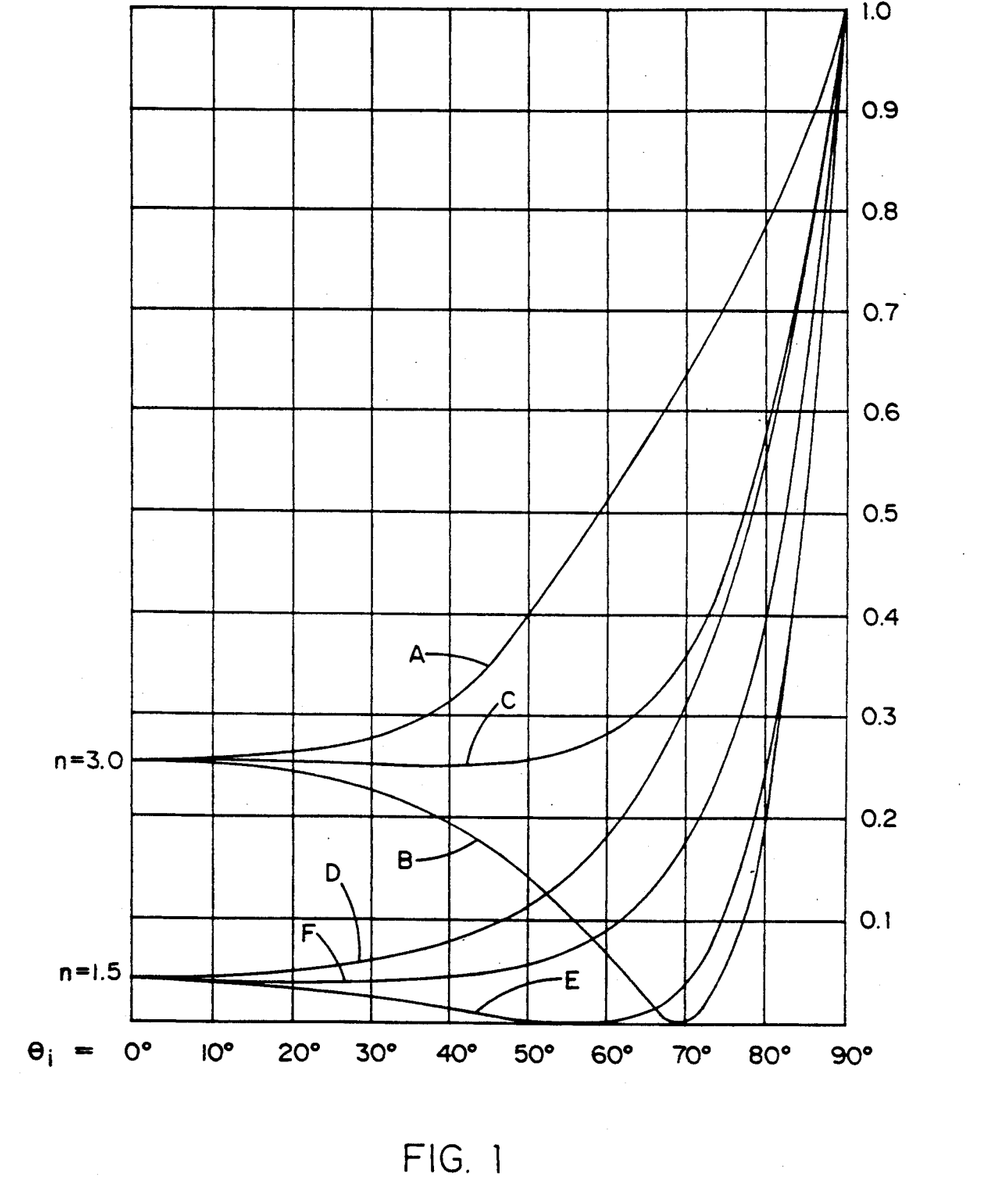
FIG. 1 is a graphical representation of the effect of polarization on reflectance values as a function of the angle of incidence of light rays.

FIG. 1 includes curves giving the reflectance percent, as a function of incidence angle, for two weakly absorbing materials which have refractive indices (n), respectively, of 3.0 and 1.5. In each case, the upper and lower curves correspond, respectively, to radiation polarized perpendicular to, and radiation polarized parallel to, the plane of incidence. The middle curve is the average of these two. For the material having a refractive index of 3.0, the line A represents the perpendicular polarization vector ("s" state), the line B represents the parallel polarization vector ("p" state), and the line C represents the average of curves A and B. For the material having a refractive index of 1.5, the line D represents the "s" state polarization, the line E represents the "p" state polarization, and the line F represents the average of curves D and E. The values along the X axis of the graph represent the angle of incidence. In other words, at the left of the graph, the 0° value indicates a direction perpendicular to the surface. The values along the Y axis of the graph represent reflectance, which approaches 100% as the angle of incidence approaches 90°.

As can be seen, the three curves of each set converge to the same value at normal (perpendicular) incidence (zero degrees). At this point, there is no longer a distinction between the two (s and p) polarization states. For a weakly absorbing dielectric, the reflectance at normal incidence will be simply:

$$R_s = (1-n)^2/(1+n)^2$$

Figure 2:
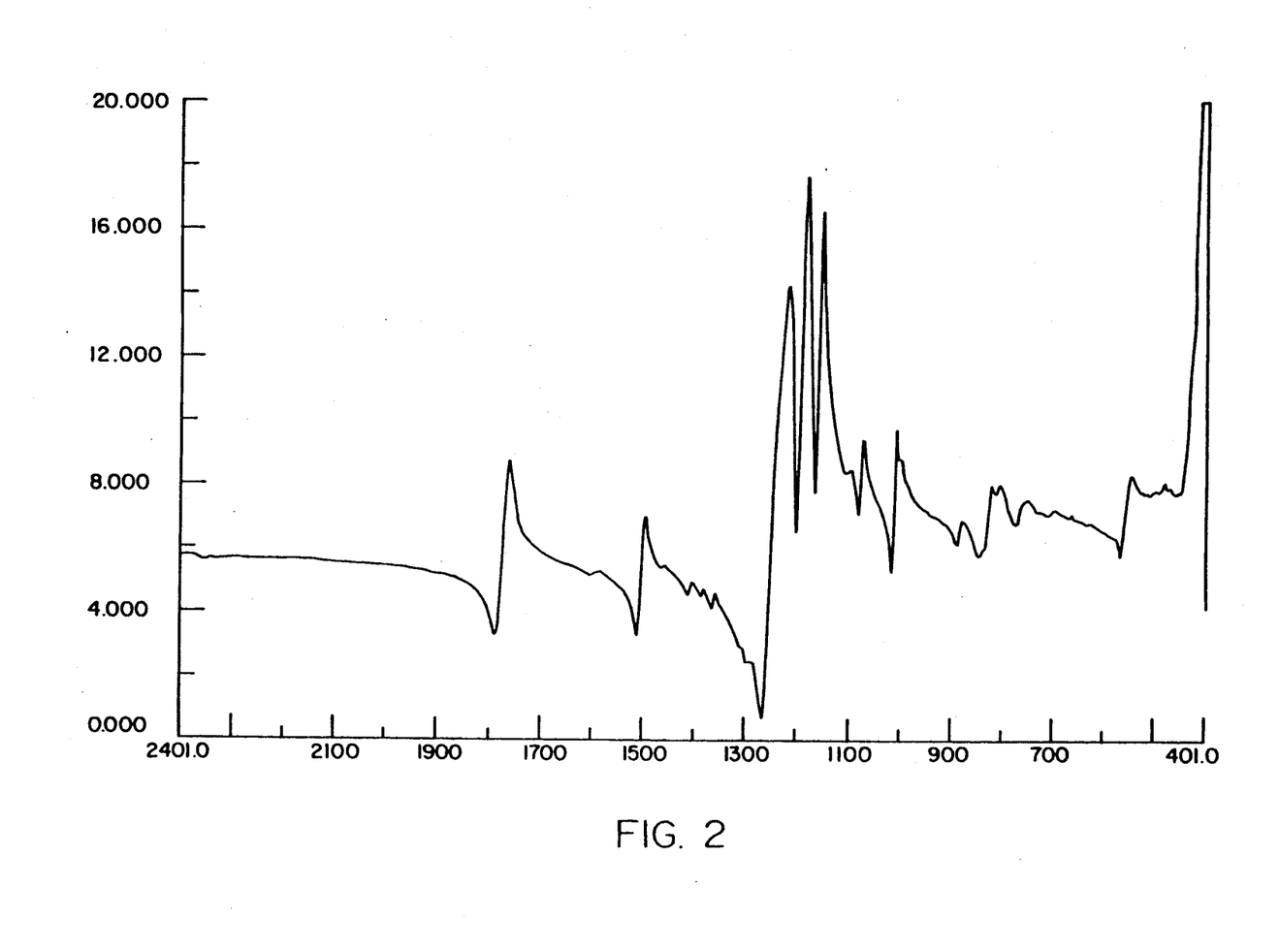
FIG. 2 is a reflectance spectrum of the material "Lexan"

For an organic material, the refractive index, and hence the reflectance, will be highly wavelength dependent. This is illustrated by FIG. 2, the specular reflectance spectrum of Lexan obtained with radiation near normal incidence. At angles other than normal incidence, the characteristics of the reflectance will be dependent on polarization and on the angle of incidence. The value of reflectance at a given wavelength will be dependent on those parameters, as well as on the value of the refractive index at that wavelength.

It follows from the above discussion that a reflectance sample device designed to yield predictable and repeatable spectra would ideally use radiation which is restricted to normal incidence. However, this is not practical, since any attempt to restrict the range of incidence angles used will also limit the signal level available for analysis. On the other hand, a reasonable approximation of this condition can be achieved if a range of angles near normal incidence is used, and if the distribution of rays is so chosen that, for a given angle of incidence, there are equal contributions from rays polarized parallel to the plane of incidence and from rays polarized perpendicular to the plane of incidence. This statement will be explained in more detail. However, its logic can be understood by inspecting FIG. 1, and noting that the average reflectance value (lines C and F) of each of the two polarization states (s & p) remains approximately equal to the value at normal incidence for a range of angles out to typically 40 or 50 degrees.

If the infrared radiation were randomly polarized, the distribution of ray directions would not matter. For each ray, the parallel ("p" state) and perpendicular ("s" state) components would be equal and, as shown in FIG. 1, the total reflectance would be approximately equal to the normal incidence value. However, this is almost never the case, since various components in a spectrometer (most notably the beamsplitter) tend to selectively favor one or another polarization state. It must be assumed that generally an unknown state of polarization will exist. In this case, it becomes important that, for the total distribution of radiation, the contribution from rays with "s" polarization states balances the contribution from rays with "p" polarization states.

Figure 3:
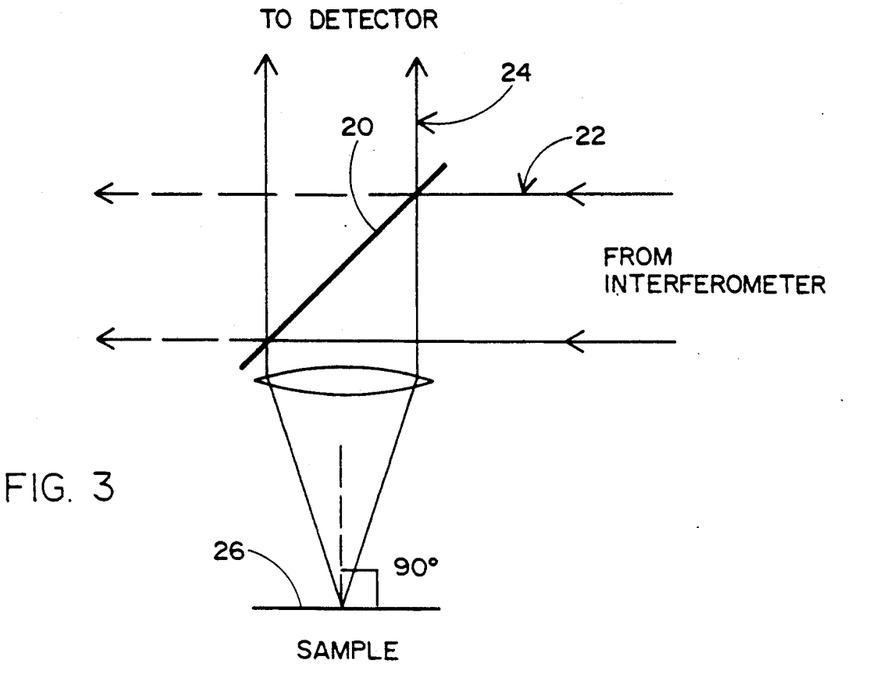
FIG. 3 is a schematic showing how a semitransparent beamsplitter might be used in normal incidence reflectance spectroscopy.

One approach to achieving the desired polarization balance would be to use a semitransparent beamsplitter 20 to separate the incoming (22) and outgoing (24) optical beams, as shown in FIG. 3. In this case, it is possible to provide radiation which is symmetrically distributed about the normal direction i.e., a line perpendicular to sample plane 26. Of course, the beamsplitter would tend to act as a polarizer. But the symmetrical distribution of ray directions (planes of incidence) would insure that, for a given polarization state, the total contribution from "s" states would be equal to the total contribution from "p" states.

For example, if the radiation happened to be polarized in the plane of inclination of the beamsplitter (i.e., the plane of the paper in FIG. 3), it would be in a pure "p" state for rays lying in this plane. However, this same polarization state would be a pure "s" state for rays lying in a plane perpendicular to the paper. In principle, the concentrations of radiation in these two planes could be balanced.

The problem with the semitransparent beamsplitter approach resides in the fact that each ray must interact with the beamsplitter surface twice. Even the best beamsplitters will be about 40% reflecting, 40% transmitting, and 20% absorbing. Each ray will undergo one reflection from the beamsplitter and one transmission through it. Thus the total efficiency (the fraction of the light, beam 24, reaching the detector) will be the product of the transmittance and the reflectance—or about 16% at best. This is a serious limitation, particularly in view of the fact that the total specular reflectance of the sample surface will typically be only 5% to 10%.

The problem of limited beamsplitter efficiency can be obviated by using a 100% reflecting mirror intercepting half of the system aperture, and arranging for the incoming and outgoing beams to use opposite halves of the aperture. This approach was used, for example, in the microscope disclosed in Doyle U.S. Pat. No. 4,852,955, assigned to Laser Precision Corporation. In principle, it can yield an overall efficiency approaching 50%. However, the use of the "split field" beamsplitter of that patent involves a distribution of incident radiation which is asymmetrical with respect to an axis normal to the sample surface. As a result, there is no assurance that the "p" and "s" polarization states will be balanced when that beamsplitter is used.

As stated above, the present invention provides the relatively high efficiency of such "split field" beam splitting, while insuring that the contributions from "p" and "s" polarization states will be balanced under all conditions.

The objectives of this invention may be accomplished by using a split field beamsplitter consisting, in the preferred version, of three reflecting blades separated by three transmitting areas, each transmitting area being equal in size and shape to the opposing reflecting blade. The required condition is that the projection of the beamsplitter in a plane perpendicular to the propagation direction is characterized by three blades having identical areas and shapes. The projection of each blade in this plane will thus have an apex angle of 60 degrees; and the overall outline will be a circle. This condition is illustrated in FIG. 4.

Figure 4:
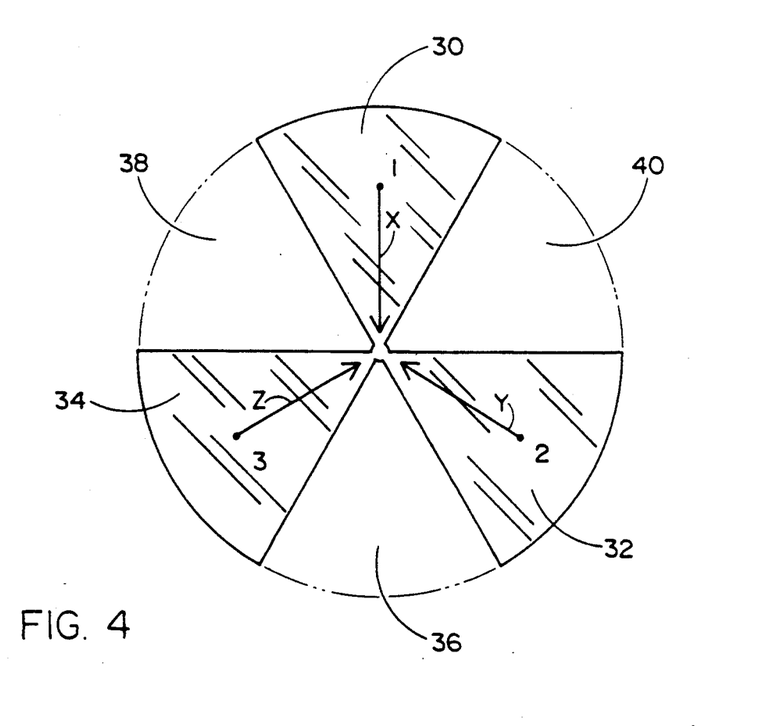
FIG. 4 is a circular projection of the desired geometry of a "split field" beamsplitter as "seen" along the radiation path.

FIG. 4 is a circular projection of the desired geometry of a split field beamsplitter 28 as "seen" along the path of the radiation beam. In other words, FIG. 4 represents the beamsplitter surface as it would appear in a plane perpendicular to the direction of the radiation beam. Three beamsplitter reflecting blades 30, 32 and 34 are shown, which have equal sizes and shapes. And three open transmitting areas 36, 38 and 40 are shown, which have equal sizes and shapes, and each of which is opposite (in the circular projection) to one of the three blades. Each blade is opposite to a transmitting area so that rays reflected toward the sample by each blade will, after specular reflection by the sample, pass through the opposite transmitting area on their path to the detector. The rays reflected by blade 30 pass through area 36; the rays reflected by blade 32 pass through area 38; and the rays reflected by blade 34 pass through area 40.

The projection seen in FIG. 4 is circular because a cylindrical collimated beam is assumed, the axis of symmetry of which would be perpendicular to, and at the center of, the circular shape. The system might be so designed that non-circular shapes would appear in the projection.

Because the entering beam from the interferometer will be at an angle to the beams reflected toward the sample, the actual reflecting shape of the beamsplitter will not be circular. Usually, the entering beam will be at right angles to the beamsplitter-reflected radiation, i.e., the beamsplitter is at a 45° angle to the radiation. The outline of the beamsplitter (including both reflecting and open areas) will therefore be elliptical.

Figure 5:
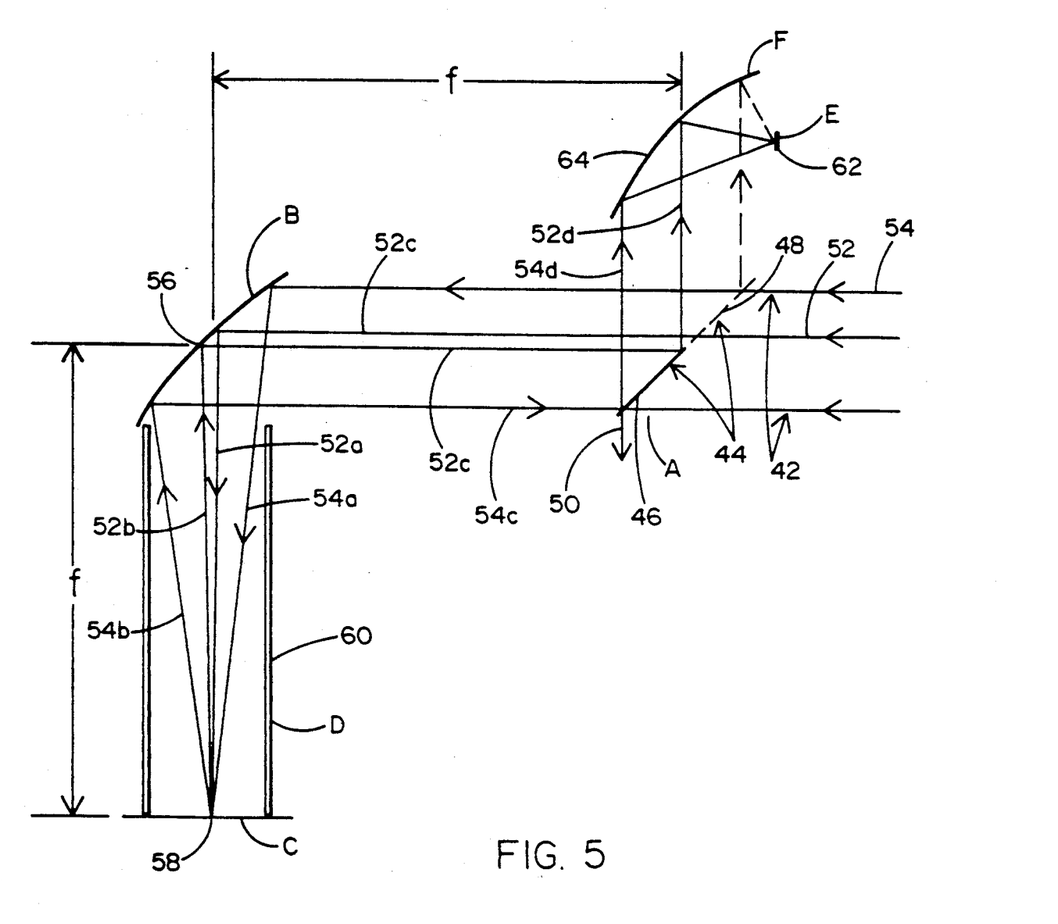
FIG. 5 is a schematic showing an example of a spectrometer system incorporating the principles of the present invention.

FIG. 5 shows schematically a possible structure for the reflecting portion of a spectrometer, in which the principles of the present invention are incorporated. A collimated beam 42 from an FTIR interferometer (not shown) is shown entering the sample area from the right side of the drawing. A beamsplitter 44 (seen along its center line) is in the path of beam 22, at a 45° angle to that path. The beamsplitter 4 is assumed to have the three-bladed design discussed above. It is further assumed that one of the blades forms the lower portion 46 of beamsplitter 44 (as seen in the figure), and that the opposed open transmitting area is at the upper, dashed-line portion 48 of beamsplitter 44. Some of the radiation in the upper portion of beam 42 will pass through the open area 48; and an equal amount of the radiation in the lower portion of beam 42 will be reflected downwardly and out of the radiation path, as evidenced by the arrow on a ray designated 50. The rays designated 52 and 54 will pass through the open area 48 on their way to the sample. Note that the reflecting blades may reflect throughput radiation either as post-sample radiation toward the detector, or as pre-sample radiation toward the sample, depending on the design of the optical system.

Beamsplitter 44 is centered at a distance "f" from a parabolic reflecting element (mirror) 56, which reflects radiation onto a sample 58. The distance "f" is the focal length of the parabolic mirror. The location of sample 58 in the focal plane of mirror 56 may be fixed by a spacing element 60, such as a length of tubing. The radiation reflected by sample 58 is directed back to mirror 56, which reflects it to the beamsplitter 44. The beamsplitter 44, which is fully reflecting, directs the returning radiation to a detector 62, via a short focal length parabolic mirror 64.

The lines and arrows are used to illustrate the path of individual rays included in the beam 42. Note that rays 52 and 54 which pass through the open area (see dashed line 48) are reflected to the detector after illuminating the sample. Thus the throughput potential is 50%. Ray 52 is reflected by mirror 56 as ray 52a toward the sample. After sample reflection, it is reflected as ray 52b back to mirror 56. It then travels as ray 52c to the reflecting blade portion 46 of beamsplitter 44, from which it is reflected as ray 52d toward detector 62. Ray 54 is reflected by the same surfaces until it reaches the detector.

In selecting the focal length mirror "f" of the paraboloid 56, it is necessary to compromise between two factors. If the focal length is too long, the system will be adversely affected by misalignment or non-flatness of the sample. If the focal length is too short, the solid angle collecting area will be large enough to collect a significant fraction of any diffusely reflected radiation which might occur. With a collecting aperture diameter of 1.25 inches, experiments indicate that focal lengths between 4 and 8 inches are suitable for most samples.

Figure 6:
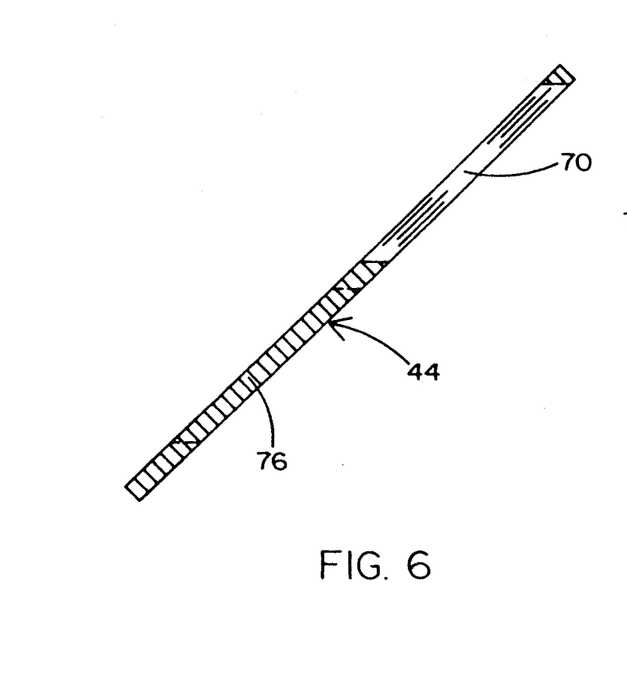
FIG. 6 is a vertical cross-section.
Figure 7:
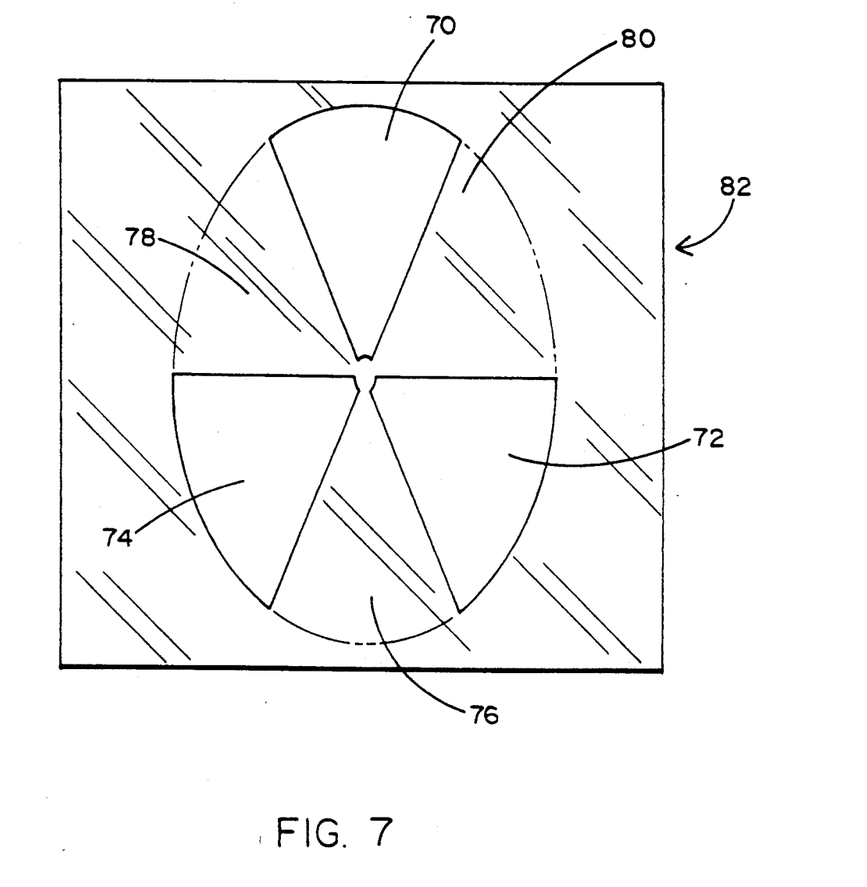
FIG. 7 is a view of the beamsplitter as a flat plate.
Figure 8:
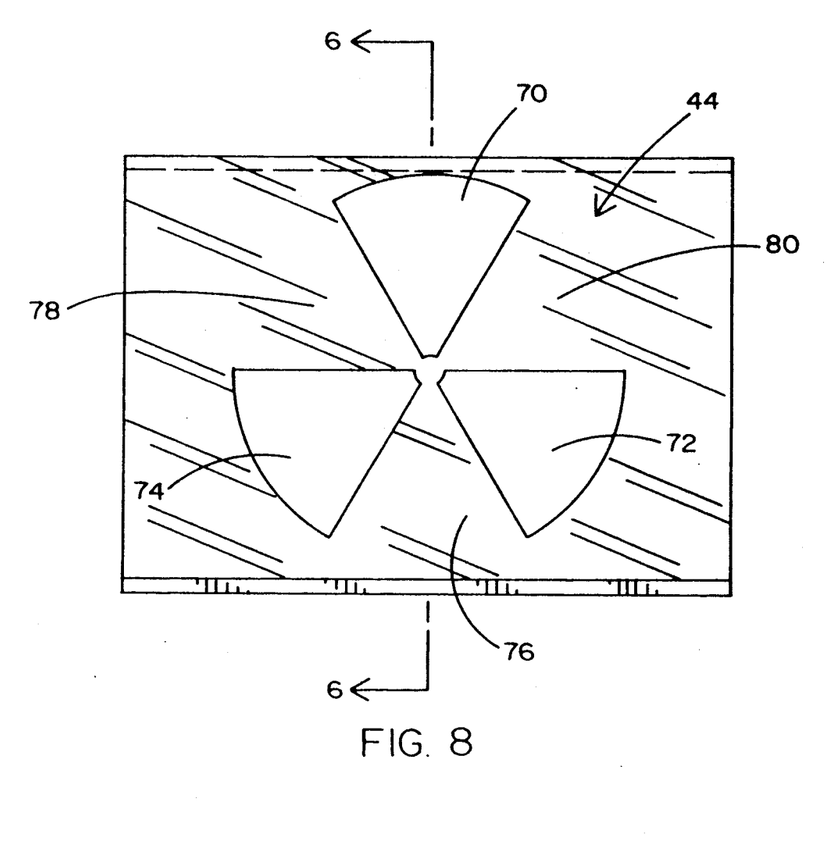
FIG. 8 is a projection of the beamsplitter in a plane perpendicular to the axis of symmetry of the radiation beam.

A description of FIGS. 6–8 will further clarify the disclosed embodiment of the invention by describing the construction of the beamsplitter. FIG. 6 is a vertical cross-section through beamsplitter 44. FIG. 7 is a view of beamsplitter 44 as a flat plate 82 formed by the manufacturer. FIG. 8 is a projection of beamsplitter 44 onto a plane perpendicular to the direction of collimated beam 54.

In the projected view (FIG. 8), the reflecting blades and open areas appear similar to those in FIG. 4. However, FIG. 4 would need to be rotated counter-clockwise 90° in order to correspond to FIG. 8. In FIG. 8, the three open areas are identified by numerals 70, 72 and 74; and the three reflecting blades are indicated at 76, 78 and 80. The outline of the blades does not appear because the entire remaining surface of the plate 82 may constitute a mirror surface.

FIG. 6 shows the upper open area 70, and the opposite blade area 76. FIG. 7 shows the actual appearance of beamsplitter plate 82 in which openings have been cut through a plate, whose remaining surface is used as a mirror.

FIG. 7 shows a beamsplitter element as it might be fabricated for use in the apparatus of the present invention. Conveniently, a rectangular (or square) flat aluminum plate 82 may be used. In order to provide the three transmitting areas, 70, 72, and 74, openings are cut through the aluminum plate. This may be done by etching. The remaining aluminum surface is then polished to provide maximum reflection at the blade areas 76, 78, and 80.

An alternative method of fabricating this beamsplitter is using a transparent plate, upon which a reflective coating is applied covering the areas which form blades 76, 78 and 80. The open transmitting areas 70, 72 and 74 would be provided by the transparency of the plate.

In FIG. 7, the shapes of the blades and transmitting areas are defined by an ellipse intersected by three straight lines. The matched shapes of upper transmitting area 70 and the opposite (lower) blade area 76 on plate 82 differ from the shapes of the other open areas and blades, because of the elliptical conformation of the overall reflecting/transmitting area. But open area 72 matches blade area 78; and open area 74 matches blade area 80.

Figure 9:
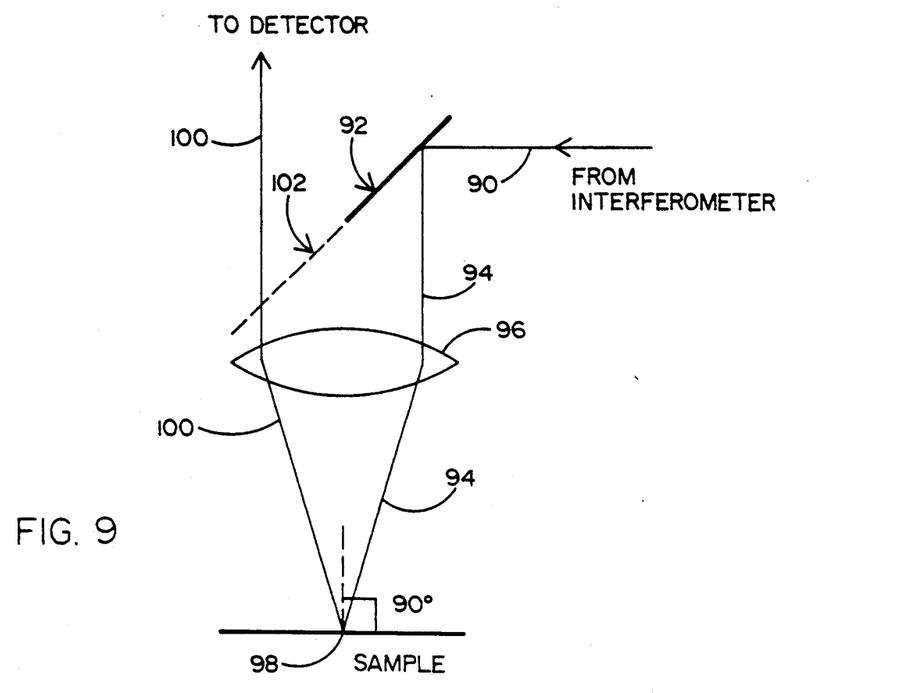
FIG. 9 shows schematically the beamsplitter combined with a focusing lens.

FIG. 9 shows schematically the beamsplitter arrangement when combined with a focusing lens. Such a lens will not generally be used in a spectrometer system because it provides lower radiation throughput than reflecting optics. However, FIG. 9 may clarify the concept of the present invention. As illustrated, the radiation entering along path 90 is reflected by a beamsplitter blade 92 along path 94. After being focused by lens 96 and reflected at sample 98, it returns along path 100, passes through lens 96, and then passes through open area 102 of the beamsplitter, on its way to the detector. Note that the beamsplitter blades may reflect the radiation either on its way to the sample, or on its return from the sample (FIG. 5). Either arrangement has the same results.

In analyzing the performance of applicant's new beamsplitter design, it is useful to recall that any arbitrary state of polarization can always be represented by its projections in any two mutually perpendicular directions. Thus, it is only required that the beamsplitter achieve the desired balanced condition for two perpendicular states of polarization.

FIG. 4 is particularly useful in this polarization analysis. First, assume that the radiation is polarized in the vertical plane of FIG. 4. Now, consider three rays (X, Y and Z) which are symmetrically positioned so as to strike the beamsplitter at the midpoints of the three blades 30, 32 and 34, respectively. The planes of incidence of these three rays at the sample are indicated by the three arrows in FIG. 4.

Represent the electric field strengths of the three rays by the vectors $E_1$, $E_2$, and $E_3$, with each field lying in the vertical plane and each having the same magnitude $E_0$. The task is first to evaluate the "p" and "s" components of the electric field for each ray, and then to calculate the total intensities of "p" and "s" state radiation, respectively. Note that intensity (I) is proportional to the square of the electric field strength (i.e., $I = E^2$).

Referring to the first ray (X) as the one striking the upper mirror segment 30, the plane of incidence of this ray will be parallel to the assumed polarization direction, i.e., $E_{1p} = E_0$ and $E_{1s} = 0$.

Figure 10A:
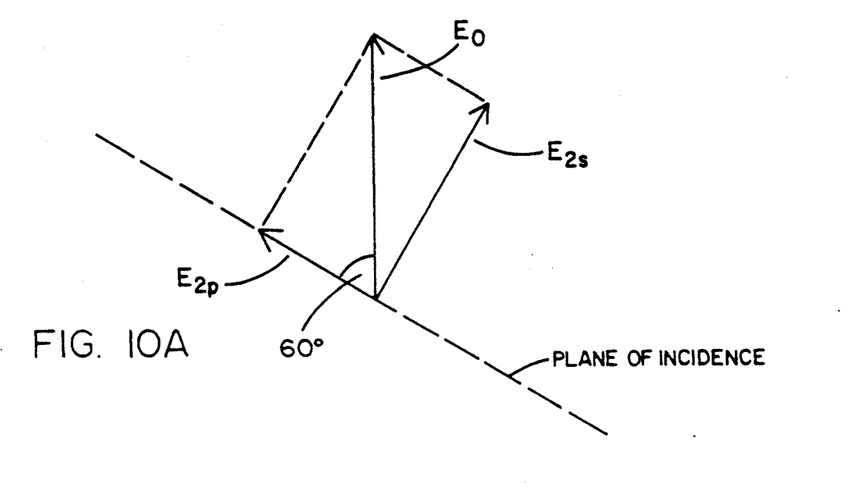
FIGS. 10A and 10B are diagrams showing vectors of the polarization states of the rays in portions of the beam.

The "p" and "s" components of the second ray (Y) can be evaluated by reference to FIG. 10A. It can be easily seen that the plane of incidence makes an angle of 60° with the plane of polarization (vertical). The components of the electric field parallel and perpendicular to the plane of incidence will thus be: $E_{2p} = E_0 \cos 60$; and $E_{2s} = E_0 \sin 60$.

Figure 10B:
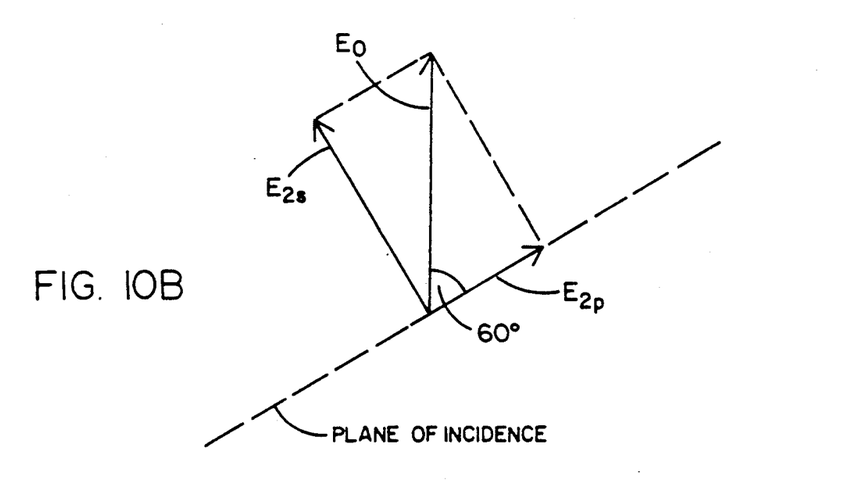

The components of the third ray (Z) have the same values. The plane of incidence of this ray also makes an angle of 60° with the vertical plane of polarization, as shown in FIG. 10B. Thus the p and s components of the third ray will be: $E_{3p} = E_0 \cos 60$; and $E_{3s} = E_0 \sin 60$.

The total of $I_p$ components are calculated as follows:

$$\begin{aligned} I_s \text{ (total)} &= I_{1p} + I_{2p} + I_{3p} \\ &= E_{1p}^2 + E_{2p}^2 + E_{3p}^2 \\ &= E_0^2 + E_0^2 \cos^2 60 + E_0^2 \cos^2 60 \\ &= E_0^2 (1 + 2\cos^2 60) \\ &= 1.5 E_0^2 \end{aligned}$$

The total of $I_s$ components are calculated as follows, arriving at the same value as the total of the $I_p$ components:

$$I_s \text{ (total)} = I_{1s} + I_{2s} + I_{3s}$$
$$= E_{1s}^2 + E_{2s}^2 + E_{3s}^2$$
$$= 0 + E_0^2 \text{Sin}^2 60 + E_0^2 \text{Sin}^2 60$$
$$= 2E_0^2 \text{Sin}^2 60$$
$$= 1.5 E_0^2$$

Thus, for the chosen polarization state, the total intensity for the three symmetrical rays will contain equal "p" and "s" contributions.

If the analysis were to start with horizontal polarization, it would lead to: $E_{1s}=E_0$ and $E_{1p}=0$. Also $E_{2s}=E_0\cos60$; and $E_{2p}=E_0\sin60$. Once again, the end result of the calculation would be $I_p$ (total) = $I_s$ (total).

For the three rays chosen, the contributions from "p" and "s" polarization are thus equal for any arbitrary polarization state.

If the analysis were to start with a ray striking some other arbitrary point on one of the beamsplitter blades, two more rays would be selected, at symmetrically placed points on the other two blades. An analysis similar to the one just given would once again prove that the polarization states are balanced. By extension, it can be stated that this is true for the sum of all of the possible rays. Therefore, the beamsplitter design meets the requirements for balanced p and s polarization.

The discussion thus far has tacitly assumed that the incoming radiation would be perfectly collimated, so that a given ray would pass through a focus on the axis as it struck the sample, and would then pass through the transmitting area of the beamsplitter at a point diagonally opposed to its starting point on a reflecting segment. In reality, the incoming beam will have a range of propagation directions. As a result, the rays which strike a given point on the beamsplitter will tend to diverge, so that by the time they return to the beamsplitter they will fall within a circular area.

Figure 11:
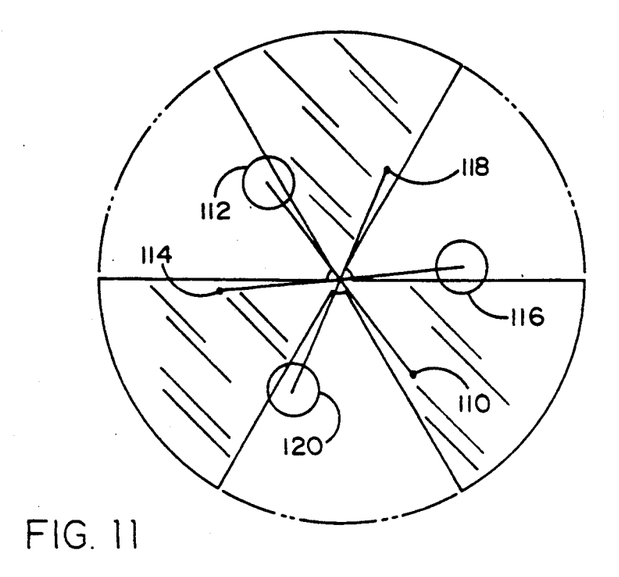
FIG. 11 shows the effect of the divergence from pre-sample to post-sample rays.

This is illustrated in FIG. 11 for three sets of balanced rays near the edges of their respective reflecting segments. In the figure, a ray striking one beamsplitter blade at point 110 will return as a bundle of rays 112 at the opposite open area; a ray striking another blade at 114 will return as a bundle of rays 116 at the opposite open area; and a ray striking the third blade at 118 will return as a bundle of rays 120 at the opposite open area. As can be seen, the beam spread results in a loss of signal due to the fact that some of the returning rays are intercepted by the reflecting blades. However, this effect is identical for all three of the ray bundles. As a result, it does not upset the polarization balance.

Similar considerations will apply to beam spread caused by surface roughness or curvature of the sample, or by failure of the sample to be properly positioned in the focal plane (the defocusing case). In most cases, the spread will be the same for all three segments; and the polarization balance will be retained. This is a direct result of the use of a three segment mirror. In other words, the three bladed design insures that any three symmetrically placed rays (i.e., rays which give the proper polarization balance) will have the same relationship to the edges of the beamsplitter blades.

Figure 12:
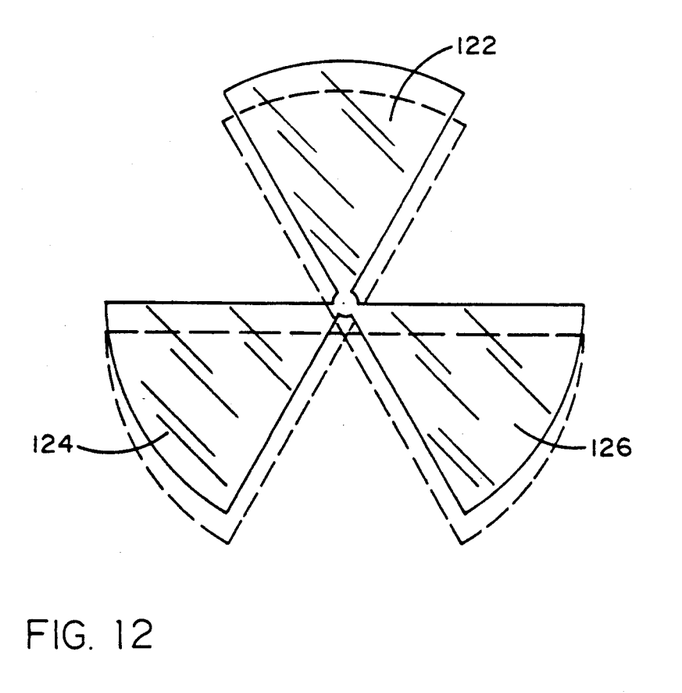
FIG. 12 shows the effect on the rays when the sample is not exactly normal to the axis of the optical system.

A particularly important non-symmetrical case is the situation that occurs when the sample is not exactly normal to the axis of the optical system. This is likely to occur in any practical application of the invention, unless extreme care is taken to control this relationship. In FIG. 12, the three segmented figure with the dashed line outline represents the radiation which has passed through the openings in the three-bladed beamsplitter and has been reflected by the sample. The solid line figure represents the reflecting blades that this radiation encounters. The offset of these two figures is caused by sample tilt. This offset results in some radiation failing to strike the reflector and thus being lost.

Again considering radiation which is polarized in the vertical plane of FIG. 12, it is seen that the radiation which misses the upper blade 122 will be predominantly in the "p" state (i.e., polarized parallel to the plane of incidence). On the other hand, radiation which misses the two lower blades 124 and 126 will be predominantly in the "s" state. Although the area of the radiation missing the lower blades is roughly twice that missing the upper blade, this radiation will have a range of incidence angles, rather than being concentrated near the maximum incidence angle. It thus can be expected that the lost radiation will be roughly balanced between the two polarization states, thus preserving the desired condition.

A calculation has been performed to determine the total reflected power lost in the three shaded regions of FIG. 12 as a function of polarization states, under the reasonable assumption that the departures of the "s" and "p" polarization contributions from the normal incidence value have positive and negative quadratic dependences on incidence angle. The absolute values of these contributions will depend on the physical constants of the material being studied. However, the calculation indicates that, for virtually any material, the departure of the "s" state power from the normal incidence value will have a magnitude about 80% of that of the "p" state. Since the first is positive, while the second is negative, they will tend to cancel. Although this cancellation is not perfect, it is still far better than would be encountered with other beamsplitters, such as a single-bladed design, in which case virtually all of the lost power would be a single polarization state.

Although the preferred embodiment of the present invention uses a three bladed beamsplitter, it is probable that the required conditions will be at least approximately met by designs having any odd number of blades greater than three. The use of an even number of blades will not work since, in that case, a ray reflected by a beamsplitter blade and then by the sample will again strike a blade.

Figure 13:
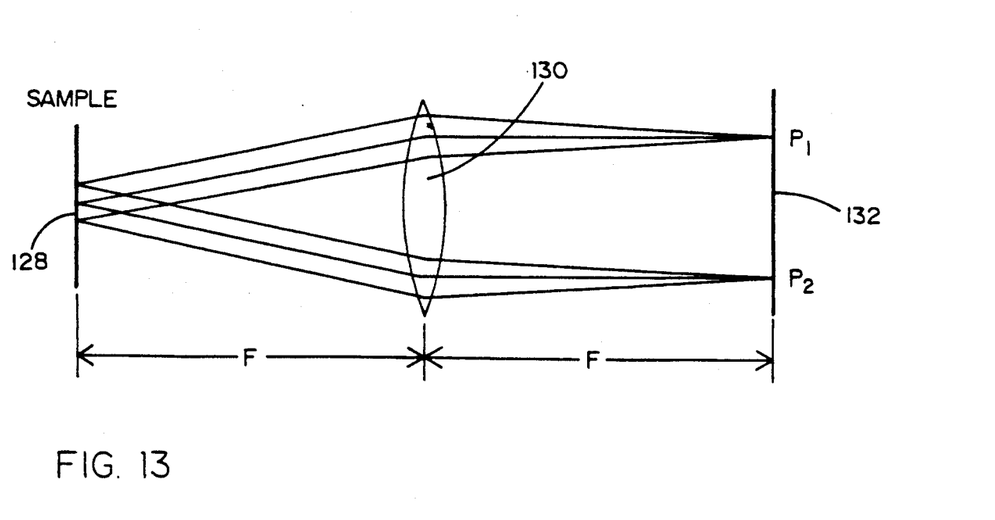
FIG. 13 is a diagram showing the beamsplitter located in a self-conjugate plane.

The loss of signal due to incomplete collimation can be mitigated by centering the beamsplitter in a self-conjugate plane, i.e., a plane which would include the image of an object located in it. This situation is illustrated in FIG. 13. Here the sample 128 is located in the focal region of a lens 130 having a focal length of "F". An object, such as point "$P_1$", located in a plane 132 a distance "F" behind the lens, will be imaged at point "$P_2$" in this same plane. Thus an edge of the beamsplitter located in this plane will be imaged as a sharp line. This provision does not alleviate beam spread arising from sample imperfections or defocusing.

From the foregoing description, it will be apparent that the apparatus and method disclosed in this application will provide the significant functional benefits summarized in the introductory portion of the specification.

The following claims are intended not only to cover the specific embodiments disclosed, but also to cover the inventive concepts explained herein with the maximum breadth and comprehensiveness permitted by the prior art.

What is claimed is:

1. A spectroscopy system for analysis of a sample, using external reflectance spectroscopy, which comprises:
   means for providing a pre-sample analytical radiation beam;
   means for detecting a post-sample analytical radiation beam;
   the analytical radiation beam comprising rays which have "p" state and "s" state polarization vectors;
   means for positioning a sample which will provide a significant amount of specular reflection; and
   a beamsplitter which (a) causes approximately half of the pre-sample radiation beam to reach the sample, (b) causes substantially the full specularly reflected radiation from the sample to reach the detecting means, and (c) ensures a substantial balance between the total "p" state polarization and the total "s" state polarization of the radiation reflected by the sample.

2. The spectroscopy system of claim 1 wherein:
   the beamsplitter has a projection in a plane perpendicular to the axis of symmetry of the radiation beam, which projection comprises a plurality of reflecting blades, and an equal number of spaced open areas;
   each beamsplitter blade being opposite one of the beamsplitter open areas, and having a radiation-facing shape and area matching the opposite open area.

3. The spectroscopy system of claim 2 in which the beamsplitter projection is generally circular.

4. The spectroscopy system of claim 3 in which the beamsplitter has a generally elliptical periphery, and is located in a plane which is not perpendicular to the axis of symmetry of the radiation beam.

5. The spectroscopy system of claim 4 in which the beamsplitter is located in a plane which is at an angle of approximately 45° to the axis of symmetry of the radiation beam.

6. The spectroscopy system of claim 3 in which the radiation beam at the beamsplitter is substantially collimated.

7. The spectroscopy system of claim 2 which also comprises:
   a focusing mirror which reflects post-beamsplitter radiation to a focus at the sample, and returns post-sample radiation to the beamsplitter.

8. The spectroscopy system of claim 7 in which the beamsplitter is located in or near its self-conjugate plane.

9. The spectroscopy system of claim 2 in which the number of beamsplitter blades is three, and the number of opposite open area is three.

10. The spectroscopy system of claim 2 in which the number of beamsplitter blades is an uneven number of at least three, and the number of opposite open areas is the same as the number of blades.

11. The spectroscopy system of claim 1 which also comprises:
    a focusing mirror which reflects post-beamsplitter radiation to a focus at the sample, and returns post-angle radiation to the beamsplitter.

12. The spectroscopy system of claim 11 in which the radiation beam at the beamsplitter is substantially collimated.

13. A spectroscopy method for analysis of a sample, using external reflections spectroscopy, which comprises:
    providing a pre-sample analytical radiation beam;
    detecting a post-sample analytical radiation beam;
    the analytical radiation beam comprising rays which have "p" state and "s" state polarization vectors;
    positioning a sample which will provide a significant amount of specular reflection; and
    using a beamsplitter to (a) cause approximately half of the pre-sample radiation beam to reach the sample, (b) cause substantially the full specularly reflected radiation from the sample to reach the detecting means, and (c) ensure a substantial balance between the total "p" state polarization and the total "s" state polarization of the radiation reflected by the sample.

14. A spectroscopy method for analysis of a sample, using external reflectance spectroscopy, which comprises:
    providing a pre-sample analytical radiation beam whose rays have "p" state; and "s" state polarization vectors;
    detecting a post-sample analytical radiation beam;
    directing the beam to the sample to provide a significant amount of specular reflection;
    splitting the beam to cause approximately half of the pre-sample radiation to reach the sample and substantially all of the specularly reflected radiation to reach the detecting means; and
    providing opposite matched beam reflecting and beam transmitting areas at the beam splitting location, in order to substantially equalize the total "p" state polarization and the total "s" state polarization.

15. The spectroscopy method of claim 14 in which the pre-sample analytical beam is a collimated beam when beam splitting occurs.

* * * * *

UNITED STATES PATENT AND TRADEMARK OFFICE
CERTIFICATE OF CORRECTION

PATENT NO. : 5,015,100
DATED : May 14, 1991
INVENTOR(S) : Walter M. Doyle

It is certified that error appears in the above-identified patent and that said Letters Patent is hereby corrected as shown below:

Column 8, line 61: Change "$I_s$" to -- $I_p$ --.

Column 12, line 6: Change "area" to -- areas --.

Column 12, line 15: Change "angle" to -- sample --.

Column 12, line 20: Change "reflections" to -- reflectance --.

Column 12, line 40: Delete the semi-colon.

Signed and Sealed this

Eighth Day of September, 1992

Attest:

DOUGLAS B. COMER

Attesting Officer

Acting Commissioner of Patents and Trademarks